US008906967B2

(12) United States Patent
Frehner et al.

(10) Patent No.: US 8,906,967 B2
(45) Date of Patent: Dec. 9, 2014

(54) SESQUITERPENES AND DERIVATIVES THEREOF FOR USE AS FEED ADDITIVES

(75) Inventors: Marco Frehner, Mont-sur-Rolle (CH); Riccardo Losa, Bière (CH); Patrick Schuepfer, Renens (CH)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 12/677,626

(22) PCT Filed: Jun. 23, 2008

(86) PCT No.: PCT/EP2008/005034
§ 371 (c)(1),
(2), (4) Date: Mar. 11, 2010

(87) PCT Pub. No.: WO2009/033515
PCT Pub. Date: Mar. 19, 2009

(65) Prior Publication Data
US 2010/0173986 A1 Jul. 8, 2010

(30) Foreign Application Priority Data

Sep. 11, 2007 (EP) .................................. 07017706
Dec. 11, 2007 (EP) .................................. 07023955

(51) Int. Cl.
| | | |
|---|---|---|
| *A61K 31/01* | (2006.01) | |
| *A61K 31/015* | (2006.01) | |
| *A23L 1/30* | (2006.01) | |
| *A23K 1/18* | (2006.01) | |
| *A23K 1/175* | (2006.01) | |
| *A23K 1/16* | (2006.01) | |

(52) U.S. Cl.
CPC ............. *A23L 1/3002* (2013.01); *A23K 1/1826* (2013.01); *A23K 1/175* (2013.01); *A23K 1/184* (2013.01); *A23K 1/1603* (2013.01); *A23K 1/1609* (2013.01)
USPC ............................. 514/762; 514/763; 514/766

(58) Field of Classification Search
None
See application file for complete search history.

(56) References Cited

U.S. PATENT DOCUMENTS

| | | | | |
|---|---|---|---|---|
| 5,952,033 | A | 9/1999 | Anantharaman et al. | |
| 6,166,067 | A * | 12/2000 | Kramer et al. | ................. 514/458 |
| 2004/0076614 | A1* | 4/2004 | Schur | .............................. 424/93.4 |
| 2005/0014827 | A1* | 1/2005 | Schur | .............................. 514/553 |

FOREIGN PATENT DOCUMENTS

| | | |
|---|---|---|
| JP | 2006-342111 | 12/2006 |
| JP | 2008-019251 | 1/2008 |
| WO | 2004/091307 | 10/2004 |
| WO | WO 2004091307 A2 * | 10/2004 |
| WO | WO 2008/074028 | 6/2008 |
| WO | WO 2008074028 A1 * | 6/2008 |

OTHER PUBLICATIONS

Database WPI Week 1993, Thomson Scientific, London, GB; AN 1993-115247, XP-002499459, and SU 1 727 773 A, Apr. 23, 1992 to Lyanders et al., (Abstract) ("Lyanders", of record).*
Obafemi et al., Antimicrobial activity of extracts and a germacranolide-type sesquiterpene lactone from Tithonia diversifolia leaf extract, African Journal of Biotechnology, vol. 5 (12), pp. 1254-1258, Jun. 16, 2006.*
Chizzola, Regular Monoterpenes and Sesquiterpenes (Essential Oils), Natural Products, 2013, pp. 2973-3008.*
International Search Report for PCT/EP2008/005034, mailed Nov. 3, 2008.
Written Opinion of the International Searching Authority for PCT/EP2008/005034, mailed Nov. 3, 2008.
Hwang et al., "Antibacterial Activity of Pinus Densiflora Leaf-Derived Components Toward Human Intestinal Bacteria", J. Microbiol. Biotechnol., vol. 12, No. 4, (2002), pp. 610-616, XP002499458.
Database WPI Week 1993 Thomson Scientific, London, GB; AN 1993-115247, "Feed Additive for Piglets—Contains Essential Oil obtd. By extn. of Bark of Siberian Fir Tree and has Bacteriostatic effect on Intestinal Flora", XP002499459.

* cited by examiner

*Primary Examiner* — Svetlana M Ivanova
(74) *Attorney, Agent, or Firm* — Nixon & Vanderhye P.C.

(57) ABSTRACT

The present invention relates to the use of sesquiterpenes and derivatives thereof as components of animal feed or feed additives for the improvement of animal performance as well as to the corresponding animal feed or feed additives containing them.

2 Claims, No Drawings

SESQUITERPENES AND DERIVATIVES THEREOF FOR USE AS FEED ADDITIVES

This application is the U.S. national phase of International Application No. PCT/EP2008/005034, filed 23 Jun. 2008, which designated the U.S. and claims priority to European Application No. 07017706.8, filed 11 Sep. 2007 and European Application No. 07023955.3, filed 11 Dec. 2007, the entire contents of each of which are hereby incorporated by reference.

The present invention relates to sesquiterpenes and derivatives thereof as components of animal feed or feed additives, as well as to compositions, feed additives and feed containing them.

The term feed or feed composition means any compound, preparation, mixture, or composition suitable for, or intended for intake by an animal.

More particular, the present invention relates to a nutraceutical composition for animals comprising as active ingredient at least one sesquiterpene, a derivative or metabolite thereof with a Log P>3, preferably >4.

The term log P means a partition coefficient or distribution coefficient. It is a measure of differential solubility of a compound in the solvents octanol and water. The octanol-water partition coefficient is a measure of the hydrophobicity and hydrophilicity of a substance. In accordance with the present invention it is the logarithmic ratio of the concentrations of the solute in said solvents. There are many log P calculators or predictors available both commerically and for free, for example from www.logp.com.

The term "nutraceutical" as used herein denotes a usefulness in both the nutritional and pharmaceutical field of application. Thus, the nutraceutical compositions can find use as a complete animal feed (diet), as supplement to animal feed (feed additive), and as pharmaceutical formulations for enteral or parenteral application which may be solid formulations, or liquid formulations.

The term animal includes all animals including human. Examples of animals are non-ruminants, and ruminants. Ruminant animals include, for example, animals such as sheep, goat, and cattle, e.g. cow such as beef cattle and dairy cows. In a particular embodiment, the animal is a non-ruminant animal. Non-ruminant animals include pet animals, e.g. horses, cats and dogs; mono-gastric animals, e.g. pig or swine (including, but not limited to, piglets, growing pigs, and sows); poultry such as turkeys, ducks and chickens (including but not limited to broiler chicks, layers); fish (including but not limited to salmon, trout, tilapia, catfish and carp); and crustaceans (including but not limited to shrimp and prawn), calves (young ruminant without functional rumen or with developing rumen).

The present inventors now surprisingly found that sesquiterpenes and derivatives thereof with a log P>3, preferably >4, have a great potential for use in animal feed, e.g. for improving the feed conversion ratio (FCR) and/or for modulation of the gut flora. Further it has been found that a composition comprising at least one sesquiterpene specified hereinabove may be used for prevention of diseases caused by *Clostridium* sp.

Therefore the present invention provides the use of said compounds and of derivatives thereof as components of animal feed or feed additives.

The invention further provides the use of these compounds and derivatives thereof for the preparation of compositions improving the performance of animals, especially having activity as modulators of the gastrointestinal microflora and which are applicable via animal feed.

The present invention further relates to the use of sesquiterpenes as hereinabove defined in the manufacture of animal feed or animal feed additive for the alleviation, cure or prevention of diseases caused by *Clostridium* sp—particularly *Clostridium perfringens*—in animals, such as poultry and mammals.

Finally, the present invention provides animal feed additives on the basis of a sesquiterpene compound according to the invention, a derivative or metabolite thereof and animal feed containing as an additive such a compound, a derivative or metabolite thereof.

Diseases caused by *Clostridium* sp are common in animal stocks of poultry, pigs, rabbits, rats and calves. There is for example, a link between the disease necrotic enteritis and the presence of *Clostridium perfringens*. Necrotic enteritis is characterized by severe inflammation and sloughing of the intestinal tracts and often occurs together with coccidiosis.

Many articles have disclosed the amount of *Clostridium perfringens* in the digestive tracts to have considerable impact on the health and growth rate of a broiler. Typical symptoms of infected birds are; ruffled feathers, noticeable depression, loss of appetite, loose/runny droppings or diarrhoea and a marked reluctancy to move. Examples of such articles are B. S. Bains (1979) "A manual for poultry diseases" (Ed. Roche, Basel Switzerland); B Köhler, K Vogel and P Starost (1979) "Nekrotisierende und Ulzerative Enteritis bei Hühnern der Mast-und Legerichtung unter Bedingungen industriemässiger Geflügelproduktion" (Mh. Vet.-Med., 32, 704-711); B Köhler, K Vogel, W Witte and H Kühn (1983) "Vergleich der Ursachen von Hospitalismus durch *Cl. perfringens, Staphylococcus aureus* und Salmonellen unter den Bedingungen der industriemässigen Geflügelproduktion und Möglichkeiten ihrer Bekämpfung", (V. Intern. Tierhyg. Symposium, 25 und 26, May 1993, Leipzig, Sammelband der Vorträge, Veterinärmedizinische Fakultät Leipzig); Th. Vissienon, U Johannsen and B Köhler (1994) "Untersuchungen zur Pathologie und Pathogenese der *Clostridium perfringens*-Typ-A-Enterotoxämie des Huhnes. 1. Versuche zur experimentellen Erzeugung der Krankheit, Versuchsansatz, klinisches Bild und Moralitätsraten", (Mh. Vet.-Med., 49, 23-28); Th. Vissienon, U Johannsen, M Solveig and B Köhler (1994) "Untersuchungen zur Pathologie und Pathogenese der *Clostridium-perfringens*-Typ-A-Enterotoxamie des Huhnes. 2. Pathomorphologische und bakteriologische Befunde nach experimenteller intraduodenaler *Cl.-perfringens*-Typ-A-Infektion" (Sporen und vegetative Keime) und Toxinapplikation (Mh. Vet.-Med., 49, 93-102).

Terpenes are widespread in nature, mainly in plants as constituents of essential oils. Their building block is the hydrocarbon isoprene ($C_5H_8$). Sesquiterpenes are a class of terpenes that consist of three isoprene units and have the molecular formula $C_{15}H_{24}$. Like monoterpenes, sesquiterpenes may be acyclic or contain rings, including many unique combinations. Biochemical modifications such as oxidation or rearrangement produce the related sesquiterpenoids.

Main feature of the compounds according to the invention is the characteristic log P ratio of at least 3, preferably of at least 4.

Sesquiterpenes and their derivatives which may be used according to the inventive principle are classified as follows:

Acyclic: Biosynthetically, when geranyl pyrophosphate reacts with isopentenyl pyrophosphate, the result is the 15-carbon farnesyl pyrophosphate which is an intermediate in the biosynthesis of sesquiterpenes such as farnesene. Oxidation can then provide sesquiterpenoids such as farnesol.

Monocyclic: With the increased chain length and additional double bond, the number of possible ways that cyclization can occur is also increased and there exist a wide variety of cyclic sesquiterpenes. In addition to common six-membered ring systems such as is found in zingiberene, a constituent of the oil from ginger, cyclization of one end of the chain to the other end can lead to macrocyclic rings such as humulene.

Bicyclic: In addition to common six-membered rings such as in the cadinenes, one classic bicyclic sesquiterpene is caryophyllene, from the oil of cloves, which has a nine-membered ring and cyclobutane ring. Additional unsaturation provides aromatic bicyclic sesquiterpenoids such as vetivazulene and guaiazulene.

Tricylic: With the addition of a third ring, the possible structures become increasingly varied. Examples include longifolene, copaene and the alcohol patchoulol.

Preferred compounds according to the present invention are disclosed in table 1.

TABLE 1

| Sesquiterpene | LogP |
|---|---|
| farnesyl acetone | 7.39 |
| farnesyl acetate | 7.16 |
| trans-trans farnesol | 6.47 |
| α-cedrene | 6.46 |
| α-cubebene | 6.43 |
| α-copaene | 6.33 |
| β-caryophyllene | 6.19 |
| γ-humulene | 6.1 |
| bisabolene/farnesene | 6.03 |
| β-humulene | 6.02 |
| (−) iso-ledene | 6.02 |
| (+) ledene | 6 |
| α-humulene (α-caryophyllene) | 5.84 |
| β-cedrene | 5.76 |
| Longifolene | 5.75 |
| Aromadendrene | 5.67 |
| allo-aromadendrene | 5.67 |
| cedryl acetate | 5.15 |
| Farnesal | 4.98 |
| α-bisabolol | 4.82 |
| Germacrone | 4.71 |
| Nerolidol | 4.65 |
| cedrene-9-ol | 4.09 |
| (−) globulol | 3.52 |
| (−) epiglobulol | 3.52 |
| Cedrol | 3.46 |

The compounds according to the invention are either commercially available or can easily be prepared by a skilled person using processes and methods well-known in the prior art. In particular, the sesquiterpene may be isolated and purified by methods known per se, e.g. from curcuma essential oil or tea tree oil.

Sesquiterpenes according to the invention and compositions containing them improve the performance of animals, viz. their general health status and during breeding their weight gain. The compounds specified hereinabove can especially be regarded as modulators of the gastrointestinal microflora of the animals which is of importance for their health status including weight gain. Positive effects with this respect may be based at least partially, on their inhibitory effects on potentially pathogenic microorganisms, e.g. on antibacterial activity. Therefore, they can be used as feed additives or for the preparation thereof and of feed by mixing or processing them with conventional animal feed or components thereof for all kinds of animals in amounts to provide the required or desired daily uptake. Preferred animals which may be in need of such additives comprise mammals, e.g. ruminants, pigs, calves, horses, pets, birds, e.g. poultry (chickens, hens, geese, ducks, turkeys), fish and zoo animals.

The sesquiterpenes or derivatives thereof may be administrated to the animals as components of a nutraceutical composition which is conventionally fed to animals. Thus, the sesquiterpenes and derivatives thereof may be suitably administered to the animals as a component of the animal feed or in their drinking water. The said compounds or derivatives may also be administrated to the animals as a component of a pharmaceutical composition.

The normal daily dosage of a compound according to the invention provided to an animal by feed intake depends upon the kind of animal and its condition. Normally this dosage should be in the range of from about 0.05 to about 10 mg, preferably from about 0.1 to about 5 mg compound per kg of feed.

In a preferred embodiment of the invention the sesquiterpene or derivative thereof being used in an amount sufficient to provide a daily dosage of 0.0125 mg per kg body weight to about 0.5 mg per kg body weight of the subject to which it is to be administered.

Sesquiterpenes or derivatives thereof may be used in combination with conventional ingredients present in an animal feed composition (diet) such as calcium carbonates, electrolytes such as ammonium chloride, proteins such as soya bean meal, wheat, starch, sunflower meal, corn, meat and bone meal, amino acids, animal fat, vitamins and trace minerals.

In a particular embodiment, the invention relates to methods for using sesquiterpenes in animal feed for improving the Feed Conversion Ratio (FCR) and/or for modulation of the gut microflora. In alternative embodiments, sesquiterpenes according to the invention improve animal feed digestibility, and/or maintain animal health by aiding in proper digestion and/or supporting immune system function.

The FCR may be determined on the basis of a broiler chicken growth trial comprising a first treatment in which the sesquiterpene according to the invention is added to the animal feed in a suitable concentration per kg feed, and a second treatment (control) with no addition of the sesquiterpene to the animal feed.

As it is generally known, an improved FCR is lower than the control FCR. In particular embodiments, the FCR is improved (i.e., reduced) as compared to the control by at least 1.0%, preferably at least 1.5%, 1.6%, 1.7%, 1.8%, 1.9%, 2.0%, 2.1%, 2.2%, 2.3%, 2.4%, or at least 2.5%.

The term "gut" as used herein designates the gastrointestinal or digestive tract (also referred to as the alimentary canal) and it refers to the system of organs within multicellular animals which takes in food, digests it to extract energy and nutrients, and expels the remaining waste.

The term gut "microflora" as used herein refers to the natural microbial cultures residing in the gut and maintaining health by aiding in proper digestion and/or supporting immune system function.

The term "modulate" as used herein in connection with the gut microflora generally means to change, manipulate, alter, or adjust the function or status thereof in a healthy and normally functioning animal, i.e. a non-therapeutic use.

Particular examples of compositions of the invention are the following:

An animal feed additive comprising (a) at least one sesquiterpene, or a derivative thereof as specified hereinabove (b) at least one fat-soluble vitamin, (c) at least one water-soluble vitamin, (d) at least one trace mineral, and/or (e) at least one macro mineral;

An animal feed composition comprising at least one sesquiterpene or a derivative thereof according to the invention and a crude protein content of 50 to 800 g/kg feed.

The so-called premixes are examples of animal feed additives of the invention. A premix designates a preferably uniform mixture of one or more micro-ingredients with diluent and/or carrier. Premixes are used to facilitate uniform dispersion of micro-ingredients in a larger mix.

For the use in animal feed, however, the at-least-one sesquiterpene need not be that pure; the corresponding composition may include other sesquiterpenes and derivatives or the at-least one sesquiterpene may be among the main 5 or 10 components of an extract which is used in animal feed.

In the present context, the term Feed Conversion Ratio, or FCR, is used synonymously with the term feed conversion. The FCR is calculated as the feed intake in g/animal relative to the weight gain in g/animal.

Further, optional, feed additive ingredients are coloring agents, e.g. carotenoids such as beta-carotene, canthaxanthin, apoester, astaxanthin, and lutein; aroma compounds; stabilisers; antimicrobial peptides; polyunsaturated fatty acids; reactive oxygen generating species; and/or at least one enzyme selected from amongst phytase (EC 3.1.3.8 or 3.1.3.26); xylanase (EC 3.2.1.8); galactanase (EC 3.2.1.89); alpha-galactosidase (EC 3.2.1.22); protease (EC 3.4.), phospholipase A1 (EC 3.1.1.32); phospholipase A2 (EC 3.1.1.4); lysophospholipase (EC 3.1.1.5); phospholipase C (EC 3.1.4.3); phospholipase D (EC 3.1.4.4); amylase such as, for example, alpha-amylase (EC 3.2.1.1); and/or beta-glucanase (EC 3.2.1.4 or EC 3.2.1.6).

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a syntethase.

Usually fat- and water-soluble vitamins, as well as trace minerals form part of a so-called premix intended for addition to the feed, whereas macro minerals are usually separately added to the feed. Either of these composition types, when enriched with sesquiterpene is an animal feed additive of the invention.

The following are non-exclusive lists of examples of these components:

Examples of fat-soluble vitamins are vitamin A, vitamin D3, vitamin E, and vitamin K, e.g. vitamin K3.

Examples of water-soluble vitamins are vitamin C, vitamin B12, biotin and choline, vitamin B1, vitamin B2, vitamin B6, niacin, folic acid and panthothenate, e.g. Ca-D-panthothenate.

Examples of trace minerals are manganese, zinc, iron, copper, iodine, selenium, and cobalt.

Examples of macro minerals are calcium, phosphorus and sodium.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

Animal feed compositions or diets have a relatively high content of protein. Poultry and pig diets can be characterized as indicated in Table B of WO 01/58275, columns 2-3. Fish diets can be characterized as indicated in column 4 of this Table B. Furthermore such fish diets usually have a crude fat content of 200-310 g/kg.

WO 01/58275 corresponds to U.S. Ser. No. 09/779,334 which is hereby incorporated by reference.

An animal feed composition according to the invention has a crude protein content of 50-800 g/kg, and furthermore comprises at least one sesquiterpene and/or at least a derivative thereof as described and/or claimed herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e. Crude protein (g/kg)=N(g/kg)×6.25. The nitrogen content is determined by the Kjeldahl method (A.O.A.C., 1984, Official Methods of Analysis 14th ed., Association of Official Analytical Chemists, Washington D.C.).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & looijen by, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one vegetable protein or protein source. It may also contain animal protein, such as Meat and Bone Meal, and/or Fish Meal, typically in an amount of 0-25%. The term vegetable proteins as used herein refers to any compound, composition, preparation or mixture that includes at least one protein derived from or originating from a vegetable, including modified proteins and protein-derivatives. In particular embodiments, the protein content of the vegetable proteins is at least 10, 20, 30, 40, 50, or 60% (w/w).

Vegetable proteins may be derived from vegetable protein sources, such as legumes and cereals, for example materials from plants of the families Fabaceae (Leguminosae), Cruciferaceae, Chenopodiaceae, and Poaceae, such as soy bean meal, lupin meal and rapeseed meal.

In a particular embodiment, the vegetable protein source is material from one or more plants of the family Fabaceae, e.g. soybean, lupine, pea, or bean.

In another particular embodiment, the vegetable protein source is material from one or more plants of the family Chenopodiaceae, e.g. beet, sugar beet, spinach or quinoa.

Other examples of vegetable protein sources are rapeseed, sunflower seed, cotton seed, and cabbage.

Other examples of vegetable protein sources are cereals such as barley, wheat, rye, oat, maize (corn), rice, triticale, and sorghum.

In still further particular embodiments, the animal feed composition of the invention contains 0-80% maize; and/or 0-80% sorghum; and/or 0-70% wheat; and/or 0-70% Barley; and/or 0-30% oats; and/or 0-30% rye; and/or 0-40% soybean meal; and/or 0-25% fish meal; and/or 0-25% meat and bone meal; and/or 0-20% whey.

Animal diets can e.g. be manufactured as mash feed (non pelleted) or pelleted feed. Typically, the milled feed-stuffs are mixed and sufficient amounts of essential vitamins and minerals are added according to the specifications for the species in question. The sesquiterpene or the derivative thereof can be added as solid or liquid formulations.

The final ["final" is intended as the "total" or the "sum of all sesquiterpenes] sesquiterpene concentration in the diet is within the range of 0.05-200 mg per kg diet, for example in the range of 0.2-10 mg per kg animal diet.

The sesquiterpene or the derivative thereof should of course be applied in an effective amount, i.e. in an amount adequate for improving feed conversion.

It is at present contemplated that the sesquiterpene is administered in one or more of the following amounts (dosage ranges): 0.01-500; 0.01-200; 0.01-100; 0.02-50, 0.05-20 0.5-100; 1-50; 5-100; 10-100; 0.05-50; 1-10; or 0.10-10, all these ranges being in mg sesquiterpene per kg feed (ppm).

The following examples further illustrate the invention, but they should not be construed as limiting the invention.

EXAMPLE 1

Animal Feed Additive

An animal feed additive is prepared by adding 1 g of at least one of a sesquiterpene selected from Table 1 to the following premix (per kilo of premix):

1100000 IE Vitamin A
300000 IE Vitamin D3
4000 IE Vitamin E
250 mg Vitamin B1
800 mg Vitamin B2
1200 mg Ca-D-Panthothenate
500 mg Vitamin B6
2.5 mg Vitamin B12
5000 mg Niacin
10000 mg Vitamin C
300 mg Vitamin K3
15 mg Biotin
150 mg Folic acid
50004 mg Cholin chloride
6000 mg Fe
3000 mg Cu
5400 mg Zn
8000 mg Mn
124 mg I
60 mg Co
29.7 mg Se
9000 mg Lasalocid Sodium (Avatec)
17.3% Ca
0.8% Mg
11.7% Na

EXAMPLE 2

Animal Feed

A broiler grower diet having the following composition (%, w/w) is prepared by mixing the ingredients. Wheat, rye and SBM 48 are available from Moulin Moderne Hirsinque, Hirsingue, France. After mixing, the feed is pelleted at a desired temperature, e.g. about 70° C. (3×25 mm).

| Wheat | 46.00 |
|---|---|
| Rye | 15.00 |
| Soy Bean Meal (SBM 48) | 30.73 |
| Soybean oil | 4.90 |
| DL-Methionine | 0.04 |
| DCP (Di-Calcium Phosphate) | 1.65 |
| Limestone | 0.43 |
| Salt | 0.15 |
| TiO2 | 0.10 |
| Animal feed additive (above) | 0.50 |

The resulting animal feed comprises 5 mg sesquiterpene per kg (5 ppm).

EXAMPLE 3

A broiler chicken feed ("starter") containing at least one of a sesquiterpene selected from Tab. 1 can be prepared by mixing the following ingredients together using a conventional mixing apparatus at room temperature.

| Ingredient | Amount (kg) |
|---|---|
| Soybean meal | 34.50 |
| Maize | 20.00 |
| Wheat | 37.80 |
| Soy oil | 3.13 |
| Minerals | 2.90 |
| Synthetic amino acids premix | 0.17 |
| Vitamins and trace elements premix | 1.00 |
| sesquiterpene premix (1.0% in wheat starch) | 0.10 |

In principle the sesquiterpene premix may contain 0.1-2% of the sesquiterpene derivative.

EXAMPLE 4

A broiler chicken feed ("grower") containing at least one of a sesquiterpene selected from Tab. 1 can be prepared by mixing the following ingredients together using a conventional mixing apparatus at room temperature.

| Ingredients | Amount (kg) |
|---|---|
| Soybean meal | 31.2 |
| Maize | 20.0 |
| Wheat | 41.3 |
| Soy oil | 3.4 |
| Minerals | 2.5 |
| Synthetic amino acids premix | 0.1 |
| Vitamins and trace elements premix | 1.0 |
| sesquiterpene premix (1% in wheat starch) | 0.1 |

In principle the sesquiterpene premix may contain 0.1-2% of the sesquiterpene derivative.

EXAMPLE 5

The Antimicrobial Activity of Sesquiterpenes of the Invention Towards *Clostridium perfringens*

The antimicrobial activity of the compounds of the invention towards *Clostridium perfringens* was determined in the following manner.

*Clostridium perfringens* ATCC 13124 (approx. 10e6 cfu) was added to culture tubes containing different amounts of the sesquiterpenes disclosed in Table 1 in a total of 6 ml of a suitable culture broth and the cultures were left to incubate with agitation at 37° C. At regular intervals during incubation, absorbance (650 nm) readings were taken to construct growth curves. The growth curves of the cultures of the invention were also compared to the growth curves of the controls by visual comparison. Where the culture broth remained clear and thus the curve flat this indicated no growth. The results are shown in Table 2.

From the results it is evident that the Sesquiterpenes of the invention have an in vitro bacteriostatic or at least a growth retarding effect on *Clostridium perfringens*.

TABLE 2

| Sesquiterpene | 100 | 30 | 10 | 6 | 2 | 1.2 | 1 | 0.5 | 0.4 | 0.3 | 0.2 |
|---|---|---|---|---|---|---|---|---|---|---|---|
| farnesyl acetone |  |  | − | − |  |  |  |  |  |  |  |
| farnesyl acetate |  |  | − | − |  |  |  |  |  |  |  |
| trans-trans farnesol |  |  | − | + |  |  |  |  |  |  |  |
| α-cedrene |  |  | − | − | − |  |  | +/− |  |  |  |
| α-cubebene | − |  |  |  | − |  |  |  | +/− |  |  |
| α-copaene | − |  |  |  | − | + |  |  |  |  |  |
| β-caryophyllene | − |  |  |  | − | +/− | +/− |  | + |  |  |
| γ-humulene |  |  |  |  | +/− |  | + |  |  |  |  |
| bisabolene/farnesene | − |  |  | − | − |  |  | +/− | + |  |  |
| β-humulene |  |  |  |  |  | − | + |  |  |  |  |
| (−) iso-ledene | − |  |  |  |  | + |  |  |  |  |  |
| (+) ledene | − |  |  |  | − | − |  |  |  |  |  |
| α-humulene (α-caryophyllene) |  |  | − | − | − |  | + | + |  |  |  |
| β-cedrene |  |  | − | − | − |  |  |  | +/− |  |  |
| Longifolene |  |  | − | − | − |  |  |  | + |  |  |
| Aromadendrene | − |  |  |  | + |  |  |  |  |  |  |
| allo-aromadendrene | − |  |  | − |  |  |  |  |  |  |  |
| cedryl acetate |  | − | − |  |  |  |  |  |  |  |  |
| Farnesal |  | +/− | + |  |  |  |  |  |  |  |  |
| α-bisabolol |  | +/− | + |  |  |  |  |  |  |  |  |
| Germacrone | − | − | + |  | + |  |  |  |  |  |  |
| Nerolidol |  | − | + |  |  |  |  |  |  |  |  |
| cedrene-9-ol |  | + | + |  |  |  |  |  |  |  |  |
| (−) globulol | − | − | + | + |  |  |  |  |  |  |  |
| (−) epiglobulol | − | − | + | + |  |  |  |  |  |  |  |
| Cedrol |  | − | + |  |  |  |  |  |  |  |  |

TABLE 2-continued

| Sesquiterpene | 100 | 30 | 10 | 6 | 2 | 1.2 | 1 | 0.5 | 0.4 | 0.3 | 0.2 |
|---|---|---|---|---|---|---|---|---|---|---|---|

The symbol "−" indicates no growth or, in the comparison, clearly lower growth than the control culture of the test organism, while "+" indicates growth or, in the comparison, similar growth to the control.

The invention claimed is:

1. A method for improving the performance of animals comprising
   providing to an animal a feed additive in an amount of 0.0125 mg per kg body weight to 0.5 mg per kg body weight per day of
   one or more selected from the group consisting of
   farnesyl acetone,
   farnesyl acetate,
   α-cedrene,
   α-cubebene,
   α-copaene,
   bisabolene,
   β-humulene,
   (−) iso-ledene,
   (+) ledene,
   β-cedrene,
   longifolene,
   aromadendrene,
   allo-aromadendrene, and
   cedryl acetate,
   wherein said feed additive is supplemented to a feed and a ratio of feed additive to feed is greater than or equal to 1 part-per-million (PPM).

2. A method for alleviating or curing diseases caused by *clostridium* sp. in animals comprising
   providing to an animal in need thereof a feed additive in an amount of 0.0125 per kg body weight to 0.5 mg per kg body weight per day of
   one or more selected from the group consisting of
   farnesyl acetone,
   farnesyl acetate,
   α-cedrene,
   α-cubebene,
   α-copaene,
   bisabolene,
   β-humulene,
   (−) iso-ledene,
   (+) ledene,
   β-cedrene,
   longifolene,
   aromadendrene,
   allo-aromadendrene, and
   cedryl acetate,
   wherein said feed additive is supplemented to a feed and a ratio of feed additive to feed is greater than or equal to 1 part-per-million (PPM).

* * * * *